United States Patent
Minter et al.

(10) Patent No.: US 10,934,539 B2
(45) Date of Patent: Mar. 2, 2021

(54) ISOLATION OF NUCLEIC ACIDS

(71) Applicant: REVOLUGEN LIMITED, Hadfield, Derbyshire (GB)

(72) Inventors: Stephen John Minter, Hadfield (GB); Georgios Patsos, Hadfield (GB)

(73) Assignee: RevoluGen Limited, Derbyshire (GB)

( * ) Notice: Subject to any disclaimer, the term of this patent is extended or adjusted under 35 U.S.C. 154(b) by 0 days.

(21) Appl. No.: 15/558,864

(22) PCT Filed: Mar. 17, 2016

(86) PCT No.: PCT/GB2016/050738
§ 371 (c)(1),
(2) Date: Sep. 15, 2017

(87) PCT Pub. No.: WO2016/147004
PCT Pub. Date: Sep. 22, 2016

(65) Prior Publication Data
US 2018/0066246 A1    Mar. 8, 2018

(30) Foreign Application Priority Data
Mar. 17, 2015    (GB) ..................................... 1504459

(51) Int. Cl.
C07H 21/00    (2006.01)
C12N 15/10    (2006.01)
C12Q 1/6806    (2018.01)

(52) U.S. Cl.
CPC ......... *C12N 15/1003* (2013.01); *C12N 15/10* (2013.01); *C12Q 1/6806* (2013.01); *C12Q 2523/32* (2013.01); *C12Q 2527/125* (2013.01); *C12Q 2527/137* (2013.01)

(58) Field of Classification Search
None
See application file for complete search history.

(56) References Cited

U.S. PATENT DOCUMENTS

| | | |
|---|---|---|
| 6,180,778 B1 | 1/2001 | Bastian et al. |
| 8,598,338 B2 | 12/2013 | Bair et al. |
| 2004/0019196 A1 | 1/2004 | Bair, Jr. et al. |
| 2005/0032105 A1 | 2/2005 | Bair et al. |
| 2006/0099605 A1* | 5/2006 | Hall, Jr. ............. C12N 15/1003 435/6.16 |
| 2007/0042384 A1 | 2/2007 | Li et al. |
| 2007/0043216 A1 | 2/2007 | Bair et al. |
| 2009/0130687 A1 | 5/2009 | Bendzko et al. |
| 2010/0297710 A1 | 11/2010 | Hoyal-Wrightson et al. |
| 2011/0251382 A1 | 10/2011 | Deggerdal et al. |
| 2013/0052721 A1 | 2/2013 | Holländer et al. |
| 2013/0053254 A1 | 2/2013 | Holländer |
| 2013/0203150 A1 | 8/2013 | Pullela et al. |
| 2014/0255943 A1 | 9/2014 | Hoyal-Wrightson et al. |

FOREIGN PATENT DOCUMENTS

| | | |
|---|---|---|
| JP | 2012080853 | 4/2012 |
| WO | WO 2004/094635 | 11/2004 |
| WO | 2005045030 | 5/2005 |
| WO | WO 2007/121717 | 11/2007 |
| WO | WO 2007/140417 | 12/2007 |
| WO | WO 2011/083429 | 7/2011 |
| WO | WO 2011/104027 | 9/2011 |
| WO | WO 2016/034892 | 3/2016 |

OTHER PUBLICATIONS

Ganaie et al. International Journal of Life Science & Pharma Research (2012), vol. 2, pp. L1-L5.*
Hong et al. J. Phycol. (1992), vol. 28, pp. 717-720.*
Lee et al. "A micro cell lysis device." Sensors and Actuators A: Physical 73.1-2 (1999): 74-79.*
International Search Report for PCT/GB2016/050738, dated Jun. 28, 2016, 3 pages.
Written Opinion of the ISA for PCT/GB2016/050738, dated Jun. 28, 2016, 7 pages.
Chan et al., "Optimisation of RNA extraction from Gracilaria changii (Gracilariales, Rhodophyta)", Journal of Applied Phycology, vol. 16, No. 4, XP019247738, Aug. 1, 2004, pp. 297-301.
Masood et al., "Inhibition of Polymerase Chain Reaction by Lithium Chloride", http://ijlpr.com/admin/php/uploads/130_pdf.pdf, vol. 2, issue 4, XP055281479, Dec. 1, 2012, pp. L1-L5.

* cited by examiner

*Primary Examiner* — Patrick T Lewis
(74) *Attorney, Agent, or Firm* — Nixon & Vanderhye, PC (57) ABSTRACT

Methods of isolating nucleic acids comprising DNA from biological material are disclosed. The methods comprise a lysis step using an aqueous composition which comprises lithium at a concentration of 0.05 to 1.0M, a chelating agent, and a surfactant to produce a lysed composition. The lysed composition is treated with a solid support that is capable of immobilising DNA in the presence of a dissolved chaotropic agent at a concentration of 0.05 to 2M and 25% to 60% by volume of a $C_{1-3}$ alkanol. The support is then washed with a first wash solution containing lithium dissolved in a $C_{1-3}$ alkanol. Subsequently, the support is washed with a liquid comprising at least 80% by volume of a $C_{1-3}$ alkanol. The nucleic acid comprising DNA is then eluted from the support.

17 Claims, 3 Drawing Sheets

Figure 1. Method_A percentage DNA recovery with error bars.

Figure 2. 0.8% agarose gel of quadruplicate Method_A and DNeasy DNA extracts. Method_A use results in higher plasmid DNA yield.

1. 10bp ladder
2. 1/100
3. 1/1000
4. 1/10,000
5. 1/100,000
6. 1/1,000,000
7. Blank Figure 3. 2% agarose gel of a representative NG titration experiment in a 300,000 HeLa cell background. Method_A DNA extracts are amplifiable down to a 1/1,000,000 dilution (~30 cells produces a faint band).

Figure 4. PCR amplicons were used as analytes in the λ-exonuclease assay. NG specific signal is produced along the titration curve down to a 1/1,000,000 dilution (~30 cells).

Figure 5.

ISOLATION OF NUCLEIC ACIDS

This application is the U.S. national phase of International Application No. PCT/GB2016/050738 filed 17 Mar. 2016, which designated the U.S. and claims priority to GB Patent Application No. 1504459.7 filed 17 Mar. 2015, the entire contents of each of which are hereby incorporated by reference.

The present invention relates to the isolation of nucleic acids comprising DNA from biological material (e.g. cells) by use of a lysis procedure and processing of the lysate to isolate the nucleic acids comprising DNA. More particularly, the invention involves the immobilisation of nucleic acids comprising DNA from the lysed biological material on a solid support and purification of the nucleic acids comprising DNA on the support prior to elution of the nucleic acids comprising DNA from the support for collection. A particular aim of the present invention is to provide a process which is relatively quick and straightforward to practise and which produces nucleic acids comprising DNA of high purity in good yield. The invention also relates to compositions for use in the lysis procedure.

The isolation of pure, intact nucleic acids comprising DNA from biological material (e.g. cells) is of importance in a number of fields, e.g. research and clinical diagnosis. Thus, purely by way of example, clinical cell-containing samples from a patient may be subjected to a procedure (including the step of cell lysis) to isolate nucleic acids comprising DNA which is then analysed by procedures well known in the art. Such analysis may be for the purpose of identifying DNA from a particular bacterium (to determine whether or not the patient has been infected by that bacterium) or may be for the purpose of whether or not the patient's DNA has one or more point mutations responsible for a medical condition.

U.S. Pat. No. 8,598,338 discloses compositions and method for using a solid support to isolate DNA from biological material (e.g. cells). The method includes at least the following steps:

(a) lysing the biological material with a buffered lysing composition containing (i) a lithium salt, e.g. lithium chloride, in a concentration of at least 1M but with a preference for much higher concentrations (up to 10M), (ii) a surface active agent which may SDS at a concentration of 0.05 to 0.2% but which is preferably a non-ionic surface active agent present at much higher concentrations (e.g. at least 5%), and (iii) an optional chelating agent;
(b) mixing the composition from (a) with a "DNA Spiking Solution" which may be either (i) a neat alcohol (e.g. methanol, ethanol or most preferably iso-propanol), or (ii) a solution of a lithium salt at a concentration of 10-15M;
(c) contacting the resultant mixture with a solid support to immobilise DNA from the lysed material;
(d) washing the support with a wash liquid containing an alcohol, and
(e) eluting the DNA.

Although not precluded from the general disclosure of U.S. Pat. No. 8,598,338 it is highly preferred that the procedure thereof is effected without the use of chaotropic agents (e.g. guanidinium salts). The procedures described in Examples 4 and 5 follow the teaching described above and use 6M LiCl lysis solution and 10M LiCl "DNA Spiking Solutions".

The procedure of U.S. Pat. No. 8,598,338 has the disadvantage that the high lithium salt concentrations used in the lysis compositions and "DNA Spiking Solutions" run the risk of contamination of the isolated DNA by lithium salt. In this regard, it is known that LiCl at 30 Mm inhibits the PCR reaction, see article entitled "Inhibition of Polymerase Chain Reaction by Lithium Chloride" authored by Ganaie et al (International Journal of Life Science & Pharma Research, Vol. 2/Issue 4, October-December 2012, Pages L1 to L5). Therefore LiCl contamination can affect downstream applications.

It is therefore an object of the present invention to obviate or mitigate the abovementioned disadvantage.

DETAILED DESCRIPTION

According to a first aspect of the present invention there is provided a method of isolating nucleic acids comprising DNA from biological material, the method comprising the steps of:

(i) effecting a lysing of the biological material with an aqueous solution which comprises a lithium at a concentration of 0.05 to 1.0M, a chelating agent, and a surfactant to produce an aqueous lysed composition,
(ii) treating the lysed composition with a solid support in the presence of a dissolved chaotropic agent at a concentration of 0.05 to 2M and 25% to 60% by volume in the liquid of a dissolved $C_{1-3}$ alkanol, said solid support being one capable of immobilising DNA,
(iii) separating the solid support from liquid,
(iv) treating the solid support with a first wash solution containing a lithium salt at a concentration of 0.05 to 1M, said first wash solution containing 20% to 90% by volume of a dissolved $C_{1-3}$ alkanol,
(v) separating the solid support from the first wash liquid,
(vi) treating the solid support with a second wash liquid which comprises at least 80% by volume of a $C_{1-3}$ alkanol, the balance if any being water,
(vii) separating the solid support from the second wash solution, and
(viii) eluting nucleic acids comprising DNA from the solid support.

Preferred features of the invention, which may be used in any combination are defined in Appendix 1 of the present specification.

The nucleic acid comprising DNA isolated by the method of the invention may incorporate RNA and may be total nucleic acid.

The invention provides excellent results in the isolation of nucleic acids comprising DNA. Contrary to the teachings of U.S. Pat. No. 8,598,338, the lysis procedures use a relatively low concentrations of lithium salt and also employ a chaotropic agent (preferably a guanidinium salt). The isolated nucleic acids comprising DNA are highly pure, there being little risk of contamination by lithium salts in view of the relatively low amounts thereof employed in the process of the invention. The method of the invention results in the isolation of substantially pure and substantially intact nucleic acids comprising DNA.

The method of the second aspect of the invention may be used for isolating nucleic acids comprising DNA (particularly genomic DNA) from a wide range of DNA-containing samples of biological origin. The sample from which the DNA is to be isolated may be, or may comprise, cells, for example animal (including mammalian) cells, plant cells, bacterial cells, or yeast or other fungal cells. Alternatively, the sample from which the DNA is to be isolated may be, or may comprise, one or more viruses. The cells, virus(es) or other DNA-containing sample from which the nucleic acids comprising DNA is to be isolated may originate from or have been present in a tissue sample or body fluids such as blood, sputum, urine or CSF In certain embodiments (e.g. for the lysis of gram negative bacteria), the method of the invention may be effected without treatment of the cells without a protease enzyme (e.g. Proteinase K) and without the need for a heating step. In other embodiments (e.g. for treatment of tissue (such as blood for the purpose of lysing whole blood cells) and for the lysis of gram positive bacteria), the sample may additionally be treated with a protease (e.g. Proteinase K). In the latter embodiments, treatment with the protease enzyme (Proteinase K) may be effective simultaneously with treatment with the lysis solution comprising lithium.

The nucleic acids comprising DNA obtained by the method of the invention are sufficiently pure to be used for the purpose of further analysis by techniques well known in the art. The DNA may be used, for example, for the purposes of research or for diagnosis of a medical condition, as required.

The method of the invention may conveniently be effected on a pellet of the biological material (e.g. cells) to be lysed. The pellet may be produced by centrifugation of a liquid sample containing the biological material, using techniques well known in the art.

In step (i) of the method of the invention for isolating nucleic acids comprising DNA from the sample of biological material (e.g. cells), the material is lysed with an aqueous composition which comprises lithium (provided by a lithium salt) in a concentration of 0.05 to 1.0 moles per litre, a chelating agent and a surfactant. The composition may comprise the stated components, may consist essentially of the stated components, or consist of these components.

The lithium salt is preferably a lithium halide, most preferably lithium chloride and is preferably present in the composition in a concentration of 0.05 to less than 1 moles per litre, preferably 0.1 to 0.9 moles per litre, more preferably 0.6 to 0.9 moles per litre, even more preferably 0.75 to 0.85 moles per litre, and most preferably about 0.8 moles per litre.

The chelating agent, which is most preferably EDTA or a salt thereof such as an alkali metal (e.g. sodium) salt, is preferably present in the composition in a concentration 1 to 20 mM per litre, more preferably 8 to 15 millimoles per litre, more preferably 9 to 11 millimoles per litre and most preferably about 10 millimoles per litre.

The surface active agent may be a non-ionic surfactant but is more preferably an anionic surfactant, most preferably SDS.

The lysis solution may have a pH of 7 to 8 but is not necessarily buffered at a pH in this range. Thus, the lysis solution may be an unbuffered composition.

In a first embodiment of carrying out the method of the invention, the material to be lysed (e.g. in the form of a pellet) may be treated with the lysis solution which comprises, consists essentially of, or consists of the components defined in step (i) of the method of the invention. The material (e.g. cells) is thoroughly admixed with the composition (e.g. by pipetting) and lysis is effected at ambient temperature for a suitable period of time. A time period of 15 to 25 minutes, e.g. about 20 minutes is generally suitable.

In accordance with this first embodiment, the lysate may then be admixed with a solution of a chaotropic agent, preferably provided by a guanidinium salt (e.g. guanidinium chloride, also known as guanidinium hydrochloride or guanidine hydrochloride), the solution of the guanidinium salt having a concentration in the range 0.05 to 1M, preferably 0.1 to 1M, more preferably 0.5 to 0.9M, and most preferably 0.6 to 0.7M. The resulting composition is then again thoroughly mixed. Ethanol (or other $C_{1-3}$ alkanol, e.g. iso-propanol) may then be added with mixing and in an amount such that the solution becomes clear. Generally the amount of ethanol (or other alkanol) will be 35% to 45% by volume, most preferably 35% to 40% by volume. Once again thorough mixing is effected. The resulting mixture then be contacted with the solid support, according to procedures described more fully in the subsequent description of this specification.

In an alternative second embodiment of the method of the invention, the aqueous lysis solution may comprise, consist essentially of, or consist of water and the other components defined for steps (i) and (ii) of the method. In this embodiment, the aqueous lysis solution may comprise, consists essentially of, or consist of water, lithium chloride at a concentration of 0.2 to 0.3M, EDTA or a sodium salt thereof at a concentration of 1 to 5 mM, guanidinium chloride at a concentration of 0.6 to 0.7M, SDS in an amount of 0.2 to 0.4% by weight and 35-40% by volume ethanol or other $C_{1-3}$ alkanol (e.g. iso-propanol)

For further embodiments of the method of the second aspect of the invention, the lysis step may be effected in the presence of the solid support. Thus, for example, any of the lysis solutions defined above may be brought into contact with the solid support and the biological material then added.

The solid support as used for the method of the invention may be a silica or silica-based material. The silica or silica-based material may be a glass, preferably a borosilicate glass. The support may comprise a fibrous material, and preferably comprises fibres of a silica or silica-based material. The filter preferably comprises borosilicate glass fibres. For preference, the support is in the form of a fibrous sheet or membrane in which the fibres are of a borosilicate glass. Filters of the type available under the designation POREX F are suitable for use in the invention. Conveniently, the solid support is provided as a filter (in the form of a sheet or membrane) in a spin tube of the type well known in the art. As indicated, the filter in the spin tube is preferably a sheet or membrane comprising borosilicate fibres. Preferably more than one such filter or sheet is provided in the spin tube. Most preferably, there are four such membrane or sheet filters (in face-to-face relationship) in the spin tube. Particularly good results are obtained where the sheet or membrane filters comprise the material available as POREX F.

The composition resulting from step (ii) of the method (which may have been effected simultaneously with step (i) may be introduced into the spin tube which is then centrifuged. During centrifugation, the nucleic acids comprising DNA (that is ultimately to be isolated) become bound to the solid support and the majority of impurities (proteins etc.) pass through the solid support (filter) and are collected in the supernatant, which may then be discarded.

In the next step of the method, the solid support is washed to remove any remaining impurities and leave substantially pure nucleic acids comprising DNA immobilised on the support. Washing is effected in two stages. In the first wash stage, the solid support is treated with a first wash liquid containing a lithium salt (preferably a lithium halide most preferably lithium chloride) in a concentration of 0.05 to 1M (preferably 0.3 to 1M, e.g. 0.3 to 0.6M, or 0.6 to 1M) and ethanol (or other $C_{1-3}$ alkanol, e.g. iso-propanol) in an amount of 45-55% by volume. The first wash liquid may, for example, be prepared by dissolving the appropriate amount of lithium salt in, say, 50% aqueous ethanol (or other $C_{1-3}$ alkanol, e.g. iso-propanol). The first wash liquid preferably consists essentially of and more preferably consists of lithium salt, ethanol (or other $C_{1-3}$ alkanol, e.g. iso-propanol) and water. We have found the combination of the lithium salt (preferably lithium chloride) and ethanol (or other $C_{1-3}$ alkanol, e.g. iso-propanol) to be particularly effective as a first wash liquid. It is most preferred that the first wash liquid contains lithium chloride in a concentration of about 400 mM to 800 mM (e.g. about 400 mM or about 800 mM) in 50% aqueous ethanol (or other $C_{1-3}$ alkanol, e.g. iso-propanol).

If the isolation procedure is being carried out in a spin tube, then the first wash liquid is added to the spin tube which is then centrifuged to cause the first wash liquid to pass through the filter and remove at least some of the remaining impurities for collection in the supernatant, which is then discarded.

A second, and usually final, wash step is then effected with a second wash liquid which comprises at least 80% by volume ethanol or other $C_{1-3}$ alkanol (e.g. iso-propanol), the balance if any being water. This second wash liquid preferably comprises (or consists essentially of or consists) about 90% by volume ethanol or other $C_{1-3}$ alkanol (e.g. iso-propanol).

In the case where the method is effected using a spin-tube, the second wash liquid is added to the spin tube which is then centrifuged to force the second wash liquid through the filter and remove remaining impurities for collection in the supernatant, which is then discarded.

At this stage, the desired nucleic acids comprising DNA are immobilised, in substantially pure form, on the solid support and can be eluted with an elution solution. The elution solution may comprise (consists essentially of or consists of) a buffered solution of EDTA or a salt thereof. A particular suitable elution solution comprises Tris-HCl in a concentration of about 10 mM, and EDTA disodium salt dihydrate at a concentration of about 0.5 mM, the solution having a pH of 9.

In the case where the method of the invention is being practised with a spin-column containing a filter on which the nucleic acids comprising DNA is immobilised, the elution solution may be added to the spin column which is then centrifuged to cause the elution solution to elute the nucleic acids comprising DNA from the solid support for collection.

The collected nucleic acids comprising DNA may then be further analysed as required.

As indicated above, the method of the invention is preferably effected using a spin tube. A typical protocol for carrying out the method of the invention is set out below:

---

Pellet cells by centrifugation and discard supernatant
Add 300 µl of aqueous lysis solution (excluding guanidinium salt and ethanol), preferably comprising 800 mM LiCl, 10 mM EDTA disodium salt dihydrate, 1% SDS) and mix well by pipetting
Incubate for 20 mins at RT
Add 350 µl of guanidinium salt solution (preferably 2M guanidinium hydrochloride stock concentration) and mix by inverting the tube or pipetting
Add 400 µl of EtOH and mix by inverting the tube or pipetting
Place 600 µl in a spin column and spin at 8,000 rpm for 1 min
Place the remaining lysate in a spin column and spin at 8,000 rpm for 1 min
Wash 1x at 8,000 rpm for 1 min with 500 µl of first wash liquid (preferably 400 mM LiCl, 50% EtOH)
Wash 1x at 14,000 rpm for 3 mins with 500 µl of second wash liquid (preferably 90% EtOH)
Spin 1x at 14,000 rpm for 1 min
Add 200 µl of elution buffer (preferably 10 mM Tris-HCl, 0.5 mM EDTA disodium salt dihydrate, pH 9.0) and elute at 8,000 rpm for 1 min

---

The invention has been thus far described particularly with regard to the method of isolating nucleic acids comprising DNA and the compositions of the solutions as used in this method. The invention further provides kits that may be used for practising the method to obtain nucleic acids comprising DNA.

According to a further (third) aspect of the present invention there is provided a kit for extracting genomic DNA from cells, the kit comprising in combination:

(i) an aqueous solution which comprises, consists essentially of, or consists of water, lithium chloride at a concentration of 0.7 to 0.9 moles per litre, EDTA or a sodium salt thereof at a concentration of 5 to 15 mM, and 0.9 to 1.1% by weight SDS, (ii) an aqueous solution of a guanidinium salt, (preferably about 2M of stock concentration of which 350 µl may be used in a final volume of 1050 µl), (iii) optionally, but preferably ethanol or other $C_{1-3}$ alkanol (e.g. iso-propanol), (iv) optionally, but preferably a first wash liquid containing lithium chloride in a concentration of 0.3 to 0.6M, said first liquid containing ethanol or other $C_{1-3}$ alkanol (e.g. iso-propanol) in an amount of 45% to 55% by volume, (v) optionally, but preferably a second wash liquid which comprises at least 80% by weight ethanol or other $C_{1-3}$ alkanol (e.g. iso-propanol), the balance if any being water, (vi) optionally, but preferably an elution buffer, and (vii) a spin column having a filter for immobilising nucleic acids comprising DNA.

The kit of the third aspect of the invention comprises at least (i), (ii) and (vii). Other reagents may be sourced separately by the user. However for convenience the kit preferably further comprises at least the first wash liquid. Additionally the kit preferably further comprises at least the elution buffer. Additionally the kit preferably further comprises at least the second wash liquid. Additionally the kit preferably further comprises the ethanol or other $C_{1-3}$ alkanol (e.g. iso-propanol) which may be absolute ethanol or other $C_{1-3}$ alkanol. The reagents and components of the kit may be as described more fully above.

In a modification of the kit of the third aspect of the invention, the modified kit may include an aqueous ethanolic (or other $C_{1-3}$ alkanoic) solution of the guanidinium salt (i.e. combining (ii) and (iii) above).

According to a fourth aspect of the present invention there is provided a kit for extracting genomic nucleic acids comprising DNA from cells, the kit comprising in combination:

(i) an aqueous solution which comprises, consist essentially of, or consists of lithium chloride in a concentration of 0.2 to 0.3 moles per litre, EDTA or a sodium salt thereof in a concentration of 1 to 5 millimoles per litre, SDS in an amount of 0.2-0.4% by weight, a guanidinium salt having a concentration of 0.6 to 0.7M and ethanol or other $C_{1-3}$ alkanol (e.g. iso-propanol) in an amount of 35-45% by volume, (ii) optionally, but preferably a first wash liquid containing lithium chloride in a concentration of 0.3 to 0.6M, said first liquid containing ethanol in an amount of 45% to 55% by volume, (iii) optionally, but preferably a second wash liquid which comprises at least 80% by weight ethanol or other $C_{1-3}$ alkanol (e.g. iso-propanol), the balance if any being water, (iv) optionally, but preferably an elution buffer, and (v) a spin column having a filter for immobilising nucleic acids comprising DNA.

The kit of the fourth aspect of the invention comprises at least (i) and (v). Other reagents may be sourced separately by the user. However for convenience the kit preferably further comprises at least the first wash liquid. Additionally the kit preferably further comprises at least the elution buffer. Additionally the kit preferably further comprises at least the second wash liquid. The reagents and components of the kit may be as described more fully above.

According to a fifth aspect of the present invention there is provided an aqueous lysis composition which comprises, consists of, or consists essentially of an aqueous solution containing a lithium salt at a concentration of 0.5 to 1.0M, a chelating agent, and a surfactant.

The invention will now be illustrated with reference to the following non-limiting Examples 1-5 and FIGS. 1-5 of the accompanying drawings.

In Examples 1-4, reference is made to "Method_A". This is a procedure in accordance with the invention and was carried out in accordance with the following protocol.

(a) Pellet cells by centrifugation and discard supernatant
(b) Add 300 µl of lysis solution (800 mM LiCl, 10 mM EDTA disodium salt dihydrate, 1% SDS) and mix well by pipetting
(c) Incubate for 20 mins at Room Temperature
(d) Add 350 µl of 2M Guanidine hydrochloride and mix by inverting the tube or pipetting
(e) Add 400 µl of EtOH and mix by inverting the tube or pipetting
(f) Place 600 µl in a spin column (with 4 POREX F filters) and spin at 8,000 rpm for 1 min
(g) Place the remaining lysate in a spin column and spin at 8,000 rpm for 1 min
(h) Add 500 µl of first wash liquid (400 mM LiCl, 50% EtOH) and spin at 8,000 rpm for 1 min
(i) Add 500 µl of second wash liquid (400 mM LiCl, 90% EtOH) and spin at 14,000 rpm for 3 mins
(j) Spin at 14,000 rpm for 1 min
(k) Add 200 µl of elution buffer (10 mM Tris-HCl, 0.5 mM EDTA disodium salt dihydrate dihydrate, pH 9.0) and elute at 8,000 rpm for 1 min Example 1

IVD Use

Method_A was developed for in vitro diagnostic (IVD) use, primarily targeting STI's such as *Neisseria gonorrhoea* (NG) *Chlamydia trachomatis* (CT), but not limited to STIs or only NG and CT.

Clinical samples used to verify Method_A's IVD potential had already being diagnosed as NG-positive, CT-positive or negative (NEG) for both NG and CT by the use of the BD Viper system which tests for the presence of both NG and CT (numbers stand for patient identification). Approximately 10 ml of clinical urine samples were spun in sealed centrifuge buckets at 5000×g for 30 mins and the pellets were processed using Method_A. DNA extracts were used as templates in quantitative (q) and digital droplet (dd) PCR experiments using. In both experiments diagnosis deriving by the use of Method_A matched that of the BD Viper system (Table 1).

TABLE 1

Method_A DNA extracts deriving from clinical urine samples confirmed initial diagnosis by the use of qPCR and ddPCR. Ct value stands for cycle threshold qPCR value.

| | CT Result | | NG result | |
|---|---|---|---|---|
| Sample ID | qPCR (CT value) | ddPCR (copies/µl) | qPCR (CT value) | ddPCR (copies/µl) |
| NG Positive Samples | | | | |
| NG_1 | — | 0 | 26.2 | 815 |
| NG_2 | — | 0.18 | 25.63 | 1192 |
| NG_3 | — | 0 | 33.87 | 5.75 |
| NG_4 | — | 0 | 32.55 | 20.1 |
| NG_5 | — | 0 | 25.48 | 2460 |
| CT Positive Sample | | | | |
| CT_01 | 31.02 | 12.39 | — | 0 |
| NG and CT Negative sample | | | | |
| NEG_1 | — | 0 | — | 0.28 |

Example 2

Extracted DNA Percentage Recovery

Approximately $10^8$ *Neisseria gonorrhoea* (NG) lab culture cells were treated in accordance with Method_A to extract nucleic acids comprising DNA in triplicate in two independent experiments. The concentration and purity of each of the replicates was assessed by Nanodrop quantification. The average concentration and A260/A280 ratio values for each experiment were then used to calculate the average and StDev for both experiments. Purity of DNA to be used as input in assessing the DNA recovery potential of Method_A was found to be well within accepted standards (Table 2).

TABLE 2

Concentration yield and purity of samples used for percentage DNA recovery assessment.
Method_A Concentration Yield and Purity

| Concentration (ng/µl) | | A260/A280 | |
|---|---|---|---|
| Average | StDev | Average | StDev |
| 77.73333333 | 0.23570226 | 2.096666667 | 0.00942809 |

Triplicates were pooled for each of the two experiments. Each pool was used to aliquot 2, 4 and 6 µg of DNA for percentage DNA recovery experiments. In more detail, each pool was used to produce two set of triplicates to be used subsequently in two experiments per pool. In short, purified DNA samples were passed through the Method_A extraction protocol and Nanodrop pre- and post-extraction values were used to calculate percentage DNA recovery of the Method_A system. The average percentage recovery values for each of the four individual experiments were used to calculate the average and StDev for all experiments. In conclusion Method_A DNA recovery is high (80 to 90%) depending on total concentration of input DNA. Although DNA percentage recovery reduces with increasing amounts of DNA the concentration range used in this experiments (2 to 6 μg) is well over anticipated DNA concentrations deriving from clinical samples (hundreds of nanograms; data not shown) (Table 3 and FIG. 1).

TABLE 3

Method_A percentage DNA recovery.

| DNA Input | Percentage Recovery | |
|---|---|---|
| | Average | St Dev |
| 2 μg | 90.59022 | 7.4396196 |
| 4 μg | 84.20733 | 4.5165637 |
| 6 μg | 80.84856 | 4.5078996 |

Example 3

Extracted DNA Phenotype, Yield and Purity Comparison to DNeasy

Figure 1:
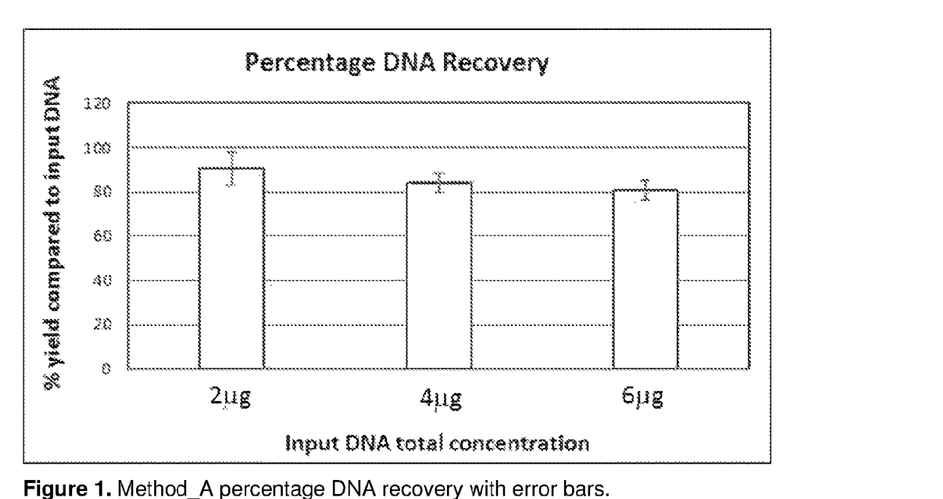
FIG. 1. Method_A percentage DNA recovery with error bars.
Figure 2:
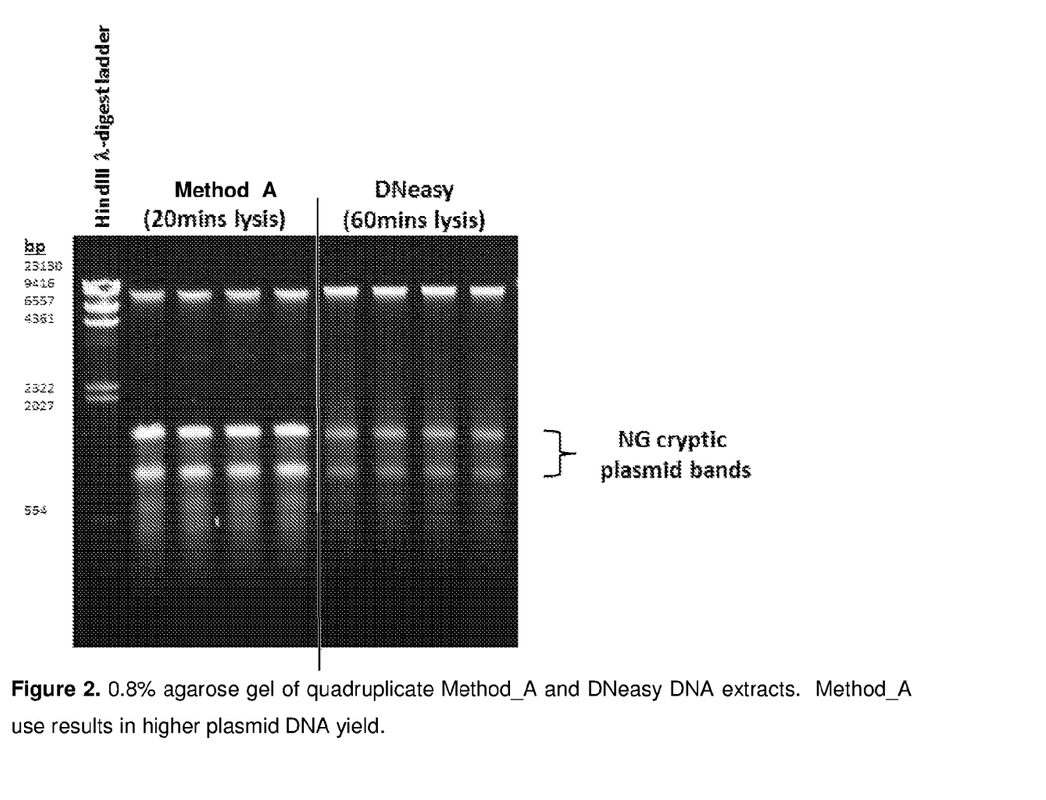
FIG. 2. 0.8% agarose gel of quadruplicate Method_A and DNeasy DNA extracts. Method_A use results in higher plasmid DNA yield.

Approximately $0.5 \times 10^8$ NG lab culture cells were treated in accordance with Method_A to extract nucleic acids comprising DNA in quadruplicate, comparing Method_A (20 mins lysis) to DNeasy (1 hr lysis) using the Gram negative extraction part of the protocol. DNeasy was chosen as a comparison standard because it is regarded as one of the best yield DNA extraction kits in the market. DNA extracted using both methods produced a very similar phenotype as judged by agarose gel electrophoresis (FIG. 2). In addition Method_A produced lower molecular weight DNA species of a greater yield than DNeasy. Purity (A260/A280) and yield were assessed by Nanodrop quantification (Table 4). Greater readings for Method_A could be explained mostly by the difference in quantity for the lower molecular weight bands. The bottom two bands on the gel are, according to the strain supplier: NCTC (Public Health England), the cryptic plasmid of NG and its supercoiled derivative. Therefore the Method_A system is particularly efficient in isolating bacterial plasmids. Bacterial plasmids are very important diagnostic targets i.e. NG antibiotic resistance, and *Chlamydia trachomatis* (CT) cryptic plasmid conserved amongst serovars. In addition, plasmid-encoded antimicrobial resistance is a widespread phenomenon for many bacterial species—see for example article authored by P. M. Bennett entitled "Plasmid Encoding Antibiotic Resistance: and Transfer of Antibiotic Resistance Genes in Bacteria (British Journal of Pharmacology (2008) 153, S347-S357).

TABLE 4

DNA yield and purity comparison between Method_A and commercial DNeasy.
Method A vs DNeasy Yield and Purity Comparison

| | Concentration (ng/μl) | | A260/A280 | |
|---|---|---|---|---|
| | Average | StDev | Average | StDev |
| method_A | 32.4 | 0.25819889 | 2.095 | 0.031091264 |
| DNeasy | 17.7 | 0.244948974 | 2.2575 | 0.073654599 |

Example 4

Sensitivity

Figure 3:
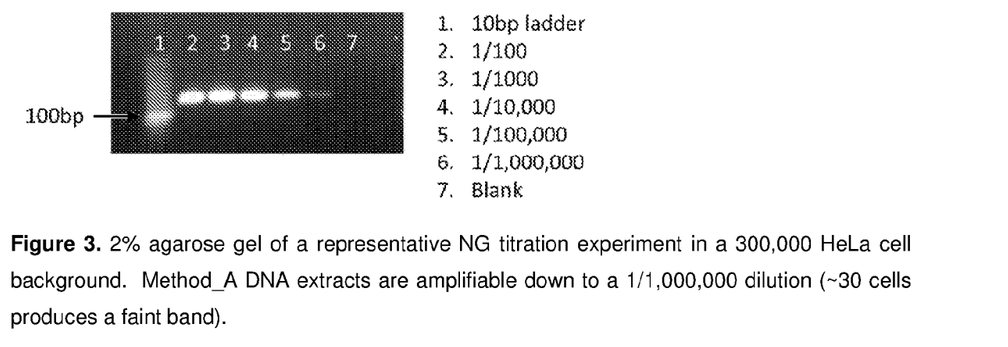
FIG. 3. 2% agarose gel of a representative NG titration experiment in a 300,000 Hela cell background. Method_A DNA extracts are amplifiable down to a 1/1,000,000 dilution (~30 cells produces a faint band).

In order to test the sensitivity of Method_A NG lab culture cells were titrated in a background of 300,000 HeLa epithelial cells, which is a very large number of nucleated cells for real urine samples (~7000 human nucleated cells are expected per ml of urine). The titrations were performed by scraping NG cells off a chocolate agar plate (O/N NG culture) and then suspending the bacteria in 1×PBS. 1/100, 1/1000, 1/10,000, 1/100,000 and 1/1,000,000 titrations of bacterial stock were prepared in quadruplicate and were spun down together with the HeLa cells, therefore spiking 300,000 HeLa cells with different numbers of NG cells. Two replicates were used to extract DNA and another two grown O/N on chocolate agar plates for total viable counts (TVC). 5 μl of each extract (total extract of 200 μl eluate) was used as a template in a PCR reaction (NG specific primers). 3 μl of amplicons were run on a 2% agarose gel (FIG. 3). Agarose gel electrophoresis cannot be used for reliable quantification of PCR amplification output, therefore a combination a TVC values and a λ-exonuclease assay (as disclosed in PCT Patent Application No. PCT/GB2015/052561) were used to calculate the number of viable NG cells that were lysed for each dilution and associate that to a quantifiable assay output. Since the chocolate agar plates were covered with a lawn of NG cells for most dilutions only the 1/1,000,000 plates and 1/100,000 dilution plates were counted and the number of cells for the rest of the dilutions were extrapolated based on these counts. The 1/1,000,000 and 1/100,000 dilution gave an average of ~30 and 300 NG cells respectively, therefore these values were used to extrapolate the number of cells for the rest of the dilutions.

Figure 4:
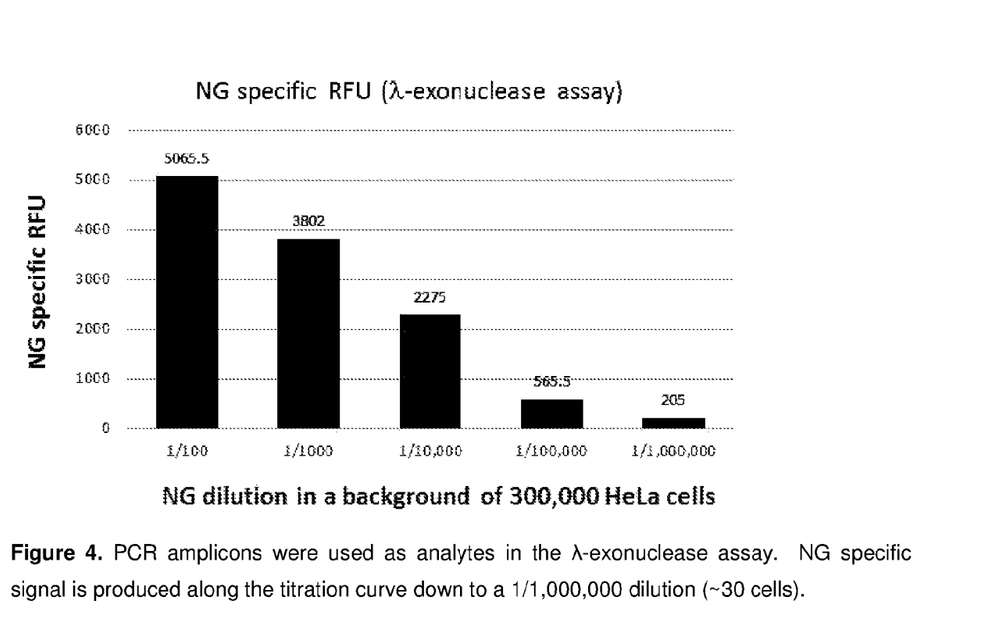
FIG. 4. PCR amplicons were used as analytes in the A.-exonuclease assay. NG specific signal is produced along the titration curve down to a 1/1,000,000 dilution (~30 cells).

In addition, the λ-exonuclease assay is a highly-specific isothermal amplification enzymatic assay that can accept PCR amplicons as analytes. The output of this assay is directly proportional to the initial amount of analyte as monitored by real-time readings on a fluorescence plate reader. Due to its high specificity, quantification is only relevant to the target sequence only and not non-specific amplified sequences, primer-dimers etc. In this particular assay an NG conserved region that would be present in the amplicon was interrogated (FIG. 4). After 30 mins of incubation at 37C RFU values were read at a plate reader background fluorescence (blank PCR sample) was subtracted from all samples. In conclusion, the Method_A system can be used to extract PCRable DNA from a few tens to hundreds (lower sensitivity at about ~30 to 300) of bacterial cells against a high background of human nucleated cells.

Example 5

This Example uses the following procedure ("Method_B") to extract nucleic acid comprising DNA from pelleted cells.

1. Add 300 μL of lysis solution (0.8M LiCl, 10 mM EDTA, 1% SDS) to the pellet and pipette thoroughly.
2. Add 20 μL of Proteinase K (20 mg/mL stock solution) and vortex for 5 secs.
3. Incubate at 56° C. for 20 minutes.
4. Add 350 μL of (2M Guanidine hydrochloride) and vortex for 5 secs.
5. Add 400 μL of Ethanol and vortex for 5 secs.
6. Add 600 μL of the resulting solution to the spin column.
7. Centrifuge at 8,000 to 11,000 rpm for 1 minute.
8. Discard the flow-through.
9. Add the remainder of the sample to the spin column.
10. Centrifuge at 8,000 to 11,000 rpm for 1 minute.
11. Discard the flow-through.
12. Add 500 μL of first wash liquid (0.8M LiCl in 50% ethanol) to the spin column.
13. Centrifuge at 8,000 rpm for 1 minute.
14. Discard the flow-through.
15. Add 500 μL of second wash liquid (90% ethanol) to the spin column.
16. Centrifuge at 14,000 rpm for 3 minutes.
17. Discard the flow-through.
18. Centrifuge the spin column at 14,000 rpm for 1 minute.
19. Discard the flow-through.
20. Add 100 to 200 μL of elution buffer (10 mM Tris-HCl, 0.5 mM EDTA, pH9.0) to the spin column.
21. Incubate at room temperature for 1 minute.
22. Elute at 8,000 rpm for 1 minute into 1.5 mL Eppendorf tubes.

Loading speeds can vary (8000 to 11000 rpm) depending on sample density

Figure 5:
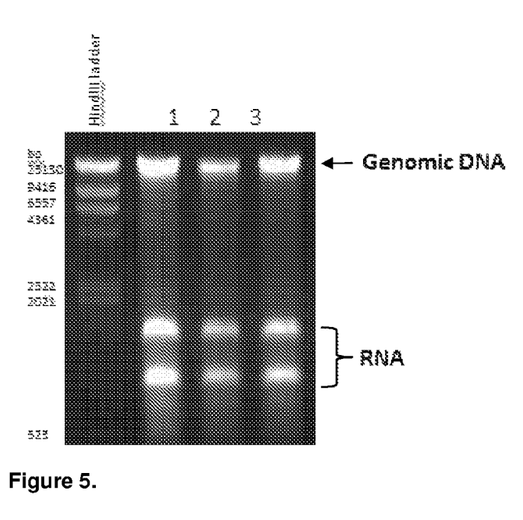
FIG. 5. Method_B was used to extract nucleic acid comprising DNA from 109 *Escherichia coli* cells and 5 µl of extracts were loaded onto a 1% ethidium bromide agarose gel together with a Hind III ladder.

EB elution volumes can vary (100 to 200 μL) depending on how concentrated extract needs to be Method_B was used to extract nucleic acid comprising DNA from 10° *Escherichia coli* cells and 5 μl of extracts were loaded onto a 1% ethidium bromide agarose gel together with a Hind III ladder. The results are shown in FIG. 5. All replicates exhibited a high molecular weight genomic DNA band together with the typical RNA phenotype.

2 ml of extracts were also quantified by nanodrop spectrophotometry and the results are shown in Table 5 below.

TABLE 5

| Replicate number | Nucleic acid concentration (ng/μl) | A260/A280 | A260/A230 |
|---|---|---|---|
| 1 | 179.5 | 2.06 | 2.28 |
| 2 | 95.5 | 2.12 | 2.71 |
| 3 | 107.7 | 2.04 | 2.23 |

APPENDIX

Embodiments of the present invention are defined in the following paragraphs.

1. A method of isolating nucleic acids comprising DNA from biological material, the method comprising the steps of:
(i) effecting a lysing of the biological material with an aqueous solution which comprises lithium at a concentration of 0.05 to 1.0M, a chelating agent, and a surfactant to produce an aqueous lysed composition,
(ii) treating the lysed composition with a solid support in the presence of a dissolved chaotropic agent at a concentration of 0.05 to 2M and 25% to 60% by volume in the liquid of a dissolved $C_{1-3}$ alkanol, said solid support being one capable of immobilising DNA,
(iii) separating the solid support from liquid,
(iv) treating the solid support with a first wash liquid containing lithium at a concentration of 0.05 to 1M, said first wash liquid containing 20% to 90% by volume of a dissolved $C_{1-3}$ alkanol,
(v) separating the solid support from the first wash liquid,
(vi) treating the solid support with a second wash liquid which comprises at least 80% by volume of a $C_{1-3}$ alkanol, the balance if any being water,
(vii) separating the solid support from the second wash solution, and
(viii) eluting nucleic acids comprising DNA from the solid support.

2. A method as defined in embodiment 1 wherein the lysis solution comprises the lithium at a concentration of 0.1 to 0.9M.

3. A method as defined in embodiment 2 wherein the lysis solution comprises the lithium at a concentration of 0.2 to 0.9M.

4. A method as defined in any one of embodiments 1 to 3 wherein the lysis solution comprises the chelating agent at a concentration of 1 to 20 mM.

5. A method as defined in any one of embodiments 1 to 4 wherein the surfactant is an anionic surfactant.

6. A method as defined in embodiment 5 wherein the anionic surfactant is present in the lysis solution in an amount of 0.05 to 2.5% by weight.

7. A method as defined in embodiment 6 wherein the anionic surfactant is present in the lysis solution in an amount of 0.1 to 1.5% by weight.

8. A method as defined in any one of embodiments 1 to 7 wherein the lysis solution consists essentially of water, a lithium salt, said chaotropic agent and said chelating agent.

9. A method as defined in any one of embodiments 1 to 8 wherein the lysis solution consists of water, a lithium salt, said chaotropic agent and said chelating agent.

10. A method as defined in embodiment 8 or 9 wherein the lysis solution contains the lithium at a concentration of 0.7 to 0.9M.

11. A method as defined in any one of embodiments 8 to 10 wherein the lysis solution contains the chelating agent at a concentration of 1 to 20 mM.

12. A method as defined in any one of embodiments 8 to 11 wherein the lysis solution contains the surfactant in an amount of 0.8 to 1.2% by weight, preferably about 0.9 to 1.1% by weight, most preferably about 1% by weight.

13. A method as defined in any one of embodiments 1 to 12 wherein the chaotropic agent is present at a concentration of 0.1 to 1M, preferably 0.5-0.9M, and more preferably 0.6 to 0.7M.

14. A method as defined in any one of embodiments 1 to 13 wherein the alkanol is present, in (ii), in an amount of 30 to 50% by volume, preferably 35% to 45% by volume, and more preferably 35% to 40% by volume.

15. A method as defined in any one of embodiments 1 to 7 wherein the lysis solution consists essentially of water, a lithium salt, said chelating agent, said surfactant, said chaotropic agent and said alkanol.

16. A method as defined in any one of embodiments 1 to 7 wherein the lysis solution consists of water, a lithium salt, said chelating agent, said surfactant, said chaotropic agent and said alkanol.

17. A method as defined in embodiment 15 or 16 wherein the lithium is present in the lysis solution at a concentration of 0.1 to 0.4M, preferably 0.2 to 0.3M.

18. A method as defined in any one of embodiments 15 to 17 wherein the surfactant is an anionic surfactant and is present in the lysis solution in an amount of 0.1 to 0.5% by weight, preferably 0.2 to 0.4% by weight.

19. A method as defined in any one of embodiments 15 to 18 wherein the chelating agent is present in the lysis solution at a concentration of 1 to 5 mM.

20. A method as defined in any one of embodiments 15 to 19 wherein the chaotropic agent is present at a concentration of 0.1 to 1M, preferably 0.5-0.9M, and more preferably 0.6 to 0.7M.

21. A method as defined in any one of embodiments 15 to 20 wherein the alkanol is present, in (ii), in an amount of 30 to 50% by volume, preferably 35% to 45% by volume, and more preferably 35% to 40% by volume.

22. A method as defined in any one of embodiments 1 to 21 wherein the lithium in the lysis solution is provided by a lithium halide.

23. A method as defined in embodiment 22 wherein the lithium halide in the lysis solution is lithium chloride.

24. A method as defined in any one of embodiments 1 to 23 wherein the chaotropic agent is provided by a guanidinium salt.

25. A method as defined in embodiment 24 wherein the guanidinium salt is guanidinium chloride.

26. A method as defined in any one of embodiments 1 to 25 wherein the chelating agent in the lysis solution is EDTA or an alkali metal salt thereof.

27. A method as defined in any one of embodiments 1 to 26 wherein the alkanol for (ii) is ethanol.

28. A method as defined in any one of embodiments 1 to 28 wherein the surfactant is SDS.

29. A method as defined in any one of embodiments 1 to 28 wherein the first wash liquid consists essentially of water, and the lithium and the alkanol of the first wash liquid.

30. A method as defined in embodiment 29 wherein the first wash liquid consists of water, and the lithium and the alkanol of the first wash liquid.

31. A method as defined in embodiment 29 or 30 wherein the lithium is present in the first wash liquid at a concentration of 0.1 to 0.8M.

32. A method as defined in embodiment 31 wherein the lithium is present in the first wash liquid at a concentration of 0.3 to 0.6M, preferably about 0.4M, or 0.6M to 1M, preferably about 0.4 to 0.8M.

33. A method as defined in any one of embodiments 29 to 32 wherein the alkanol is present in the first wash liquid in an amount of 40 to 60% by volume, preferably 45 to 55% by volume, and more preferably about 50% by volume.

34. A method as defined in any one of embodiments 29 to 33 wherein the lithium in the first wash liquid is provided by a lithium halide.

35. A method as defined in embodiment 34 wherein the lithium halide in the first wash liquid is lithium chloride.

36. A method as defined in any one of embodiments 29 to 35 wherein the alkanol in the first wash liquid is ethanol.

37. A method as defined in any one of embodiments 1 to 36 wherein the second wash solution consists essentially of water and said alkanol of the second wash solution.

38. A method as defined in any one of embodiments 1 to 36 wherein the second wash solution consists of water and said alkanol of the second wash solution.

39. A method as defined in embodiment 37 or 38 wherein the second wash solution contains 80% to 95% by volume of the alkanol of the second wash liquid.

40. A method as defined in any one of embodiments 1 to 39 wherein the alkanol in the second wash liquid is ethanol.

41. A method as defined in embodiment 1 wherein the lysis solution consists essentially of water, lithium chloride at a concentration of 0.7 to 0.9M, EDTA or a sodium salt thereof at a concentration of 5 to 15 mM and 0.9 to 1.1% by weight SDS.

42. A method as defined in embodiment 41 wherein in step (ii) the chaotropic agent is guanidinium chloride at a concentration of 0.6 to 0.7M and the alkanol is ethanol present in an amount of 35-40% by volume of the liquid.

43. A method as defined in embodiment 1 wherein the lysis solution consists essentially of water, lithium chloride at a concentration of 0.2 to 0.3M, EDTA or a sodium salt thereof at a concentration of 1 to 5 mM, guanidinium chloride at a concentration of 0.6 to 0.7M, SDS in an amount of 0.2 to 0.4% by weight and 35-40% by volume ethanol.

44. A method as defined in any one of embodiments 41 to 43 wherein the first wash liquid consists essentially of water, lithium chloride at a concentration of 0.3 to 0.6M, and 45% to 55% by volume ethanol.

45. A method as defined in any one of embodiments 41 to 44 wherein the second wash liquid consist essentially of 80% to 95% by volume of ethanol and water.

46. A method as defined in any one of embodiments 1 to 45 wherein the solid support comprises silica.

47. A method as defined in any one of embodiments 1 to 46 wherein step (iii) is effected in a spin-tube in which said solid support is a filter and steps (iii), (v), (vii) and (viii) are effected with centrifugation.

48. A method as defined in embodiment 47 wherein the filter comprises borosilicate glass fibres.

49. A method as defined in embodiment 48 wherein a plurality of said filters are provided in the spin tube.

50. A method as defined in embodiment 49 wherein four filters are provided.

51. A method as defined in any one of embodiments 1 to 50 which is effected at ambient temperature throughout.

52. A method as defined in any one of embodiments 1 to 51 which is effected without vortexing.

53. A method as defined in any one of embodiments 1 to 52 wherein the biological material from which the nucleic acids comprising DNA is to be isolated comprises cells.

54. A method as defined in embodiment 53 wherein the cells are in the form of a pellet.

55. A kit for extracting nucleic acids comprising DNA from cells, the kit comprising in combination:
(i) an aqueous solution which comprises, consists essentially of, or consists of water, lithium at a concentration of 0.05 to 1.0M, a chelating agent, and a surfactant,
(ii) a solution of a chaotropic agent (preferably a guanidinium salt),
(iii) optionally but preferably a $C_{1-3}$ alkanol, e.g. ethanol,
(iv) optionally but preferably a first wash liquid containing lithium at a concentration of 0.05 to 1M and 20% to 90% by volume of a dissolved $C_{1-3}$ alkanol,
(v) optionally but preferably a second wash liquid which comprises at least 80% by volume of a $C_{1-3}$ alkanol, preferably ethanol, the balance if any being water,
(vi) optionally but preferably an elution buffer, and
(vii) a spin column having a filter for immobilising DNA.

56. A kit for extracting nucleic acids comprising DNA from cells, the kit comprising in combination:
(i) an aqueous solution which comprises, consist essentially of, or consists of, lithium at a concentration of 0.05 to 1.0M, a chelating agent, a surfactant, a chaotropic agent (e.g. a guanidinium salt) and a dissolved $C_{1-3}$ alkanol (preferably ethanol), (ii) optionally but preferably a first wash liquid containing lithium at a concentration of 0.05 to 1M and 20% to 90% by volume of a dissolved $C_{1-3}$ alkanol,
(iii) optionally but preferably a second wash liquid which comprises at least 80% by volume of a $C_{1-3}$ alkanol, preferably ethanol, the balance if any being water,
(iv) optionally but preferably an elution buffer, and
(v) a spin column having a filter for immobilising DNA.

57. A kit as defined in embodiment 55 or 56 wherein the filter comprises at least one sheet of borosilicate fibres.

58. A kit as defined in embodiment 57 wherein the filter comprises four sheets of borosilicate fibres.

59. An aqueous lysis composition which comprises, consists of, or consists essentially of an aqueous solution containing a lithium salt at a concentration of 0.5 to 1.0M, a chelating agent, and a surfactant.

60. A lysis as defined in embodiment 59 which is as defined in any one of embodiments 2 to 28.

The invention claimed is:

1. A method of isolating nucleic acids comprising DNA from biological material, the method comprising the steps of:
    (i) effecting a lysing of the biological material with an aqueous solution which comprises lithium at a concentration of 0.6 to 0.8 M, a chelating agent, and a surfactant to produce an aqueous lysed composition,
    (ii) treating the lysed composition with a solid support in the presence of a dissolved chaotropic agent at a concentration of 0.05 to 2 M and 25% to 60% by volume in the liquid of a dissolved $C_{1-3}$ alkanol, said solid support being one capable of immobilising DNA,
    (iii) separating the solid support from liquid, wherein said separation is effected in a spin-tub in which said solid support is a filter,
    (iv) treating the solid support with a first wash solution containing lithium at a concentration of 0.05 to 1 M, said first wash solution containing 20% to 90% by volume of a dissolved $C_{1-3}$ alkanol,
    (v) separating the solid support from the first wash liquid,
    (vi) treating the solid support with a second wash liquid which comprises at least 80% by volume of a $C_{1-3}$ alkanol, the balance if any being water,
    (vii) separating the solid support from the second wash solution, and
    (viii) eluting DNA from the solid support, wherein steps (iii), (v), (vii) and (viii) are effected with centrifugation.

2. A method as claimed in claim 1 wherein the lysis solution consists essentially of water, lithium chloride at a concentration of 0.7 to 0.8 M, EDTA or a sodium salt thereof at a concentration of 5 to 15 mM and 0.9 to 1.1% by weight SDS.

3. A method as claimed in claim 2 wherein in step (ii) the chaotropic agent is guanidinium chloride at a concentration of 0.6 to 0.7 M and the alkanol is ethanol present in an amount of 35-40% by volume of the liquid.

4. A method as claimed in claim 1 wherein the first wash liquid consists essentially of water, lithium chloride at a concentration of 0.3 to 0.6 M, and 45% to 55% by volume ethanol.

5. A method as claimed in claim 1 wherein the first wash liquid consists essentially of water, lithium chloride at a concentration of 0.6 to 0.8 M, and 45% to 55% by volume ethanol.

6. A method as claimed in claim 1 wherein the second wash liquid consists essentially of 80% to 95% by volume of ethanol and water.

7. A method as claimed in claim 1 wherein the solid support comprises silica.

8. A method as claimed in claim 1 wherein the filter comprises borosilicate glass fibres.

9. A method as claimed in claim 8 wherein a plurality of said filters are provided in the spin tube.

10. A method as claimed in claim 1 wherein the biological material from which the nucleic acids comprising DNA is to be isolated comprises cells.

11. A method as claimed in claim 10 wherein the cells are in the form of a pellet.

12. A kit for extracting nucleic acids comprising DNA from cells, the kit comprising in combination:
    (i) an aqueous solution which comprises, consists essentially of, or consists of water, lithium chloride at a concentration of 0.6 to 0.8 moles per litre, EDTA or a sodium salt thereof at a concentration of 5 to 15 mM, and 0.9 to 1.1% by weight SDS,
    (ii) an aqueous solution of a guanidinium salt,
    (iii) ethanol,
    (iv) a first wash liquid containing lithium chloride in a concentration of 0.3 to 0.6 M, said first liquid containing ethanol in an amount of 45% to 55% by volume,
    (v) a second wash liquid which comprises at least 80% by volume ethanol, the balance if any being water,
    (vi) an elution buffer, and
    (vii) a spin column having a filter for immobilising DNA.

13. A kit as claimed in claim 12 wherein the filter comprises at least one sheet of borosilicate fibres.

14. A kit as claimed in claim 13 wherein the filter comprises four sheets of borosilicate fibres.

15. A lysis composition which comprises water, lithium chloride at a concentration of 0.7 to 0.8 M, EDTA or a sodium salt thereof at a concentration of 5 to 15 mM and 0.9 to 1.1% by weight SDS.

16. A method of lysing biological material comprising treating the biological material with an aqueous lysis composition as claimed in claim 15.

17. A method as claimed in claim 16 wherein the biological material comprises cells.

* * * * *